United States Patent [19]
Suzuki et al.

[11] Patent Number: 5,312,761
[45] Date of Patent: May 17, 1994

[54] METHOD FOR MEASURING TRACE QUANTITY OF OXYGEN IN GAS

[75] Inventors: Takashi Suzuki; Kenkichi Itoh; Hajime Sasaki, all of Kawasaki, Japan

[73] Assignee: Nippon Sanso Kabushiki Kaisha, Tokyo, Japan

[21] Appl. No.: 674,345
[22] PCT Filed: Aug. 27, 1990
[86] PCT No.: PCT/JP90/01083
  § 371 Date: Apr. 26, 1991
  § 102(e) Date: Apr. 26, 1991
[87] PCT Pub. No.: WO91/03731
  PCT Pub. Date: Mar. 21, 1991

[30] Foreign Application Priority Data

Aug. 28, 1989 [JP] Japan .................................. 1-220956

[51] Int. Cl.$^5$ .................................................. G01N 21/76
[52] U.S. Cl. .................................... 436/136; 422/52; 422/91; 436/138; 436/166; 436/172; 436/179
[58] Field of Search .................. 422/46, 48, 52, 91; 436/136, 138, 166, 172, 179; 250/361 C

[56] References Cited

U.S. PATENT DOCUMENTS

| | | | |
|---|---|---|---|
| 3,285,703 | 11/1966 | Narita et al. | 422/52 |
| 3,332,746 | 7/1967 | Claff et al. | 422/46 |
| 3,528,779 | 9/1970 | Fontijn | 250/361 C X |
| 3,856,475 | 12/1974 | Marx | 422/46 |
| 3,984,688 | 10/1976 | Von Bargen et al. | 250/361 C |
| 4,111,659 | 9/1978 | Bowley | 422/48 |
| 4,257,777 | 3/1981 | Dymond et al. | 436/172 X |
| 4,705,543 | 11/1987 | Kertzman | 55/158 |
| 5,019,517 | 5/1991 | Coulson | 422/89 X |
| 5,021,352 | 6/1991 | Suzuki et al. | 436/136 |

FOREIGN PATENT DOCUMENTS 63-302348 12/1988 Japan .

OTHER PUBLICATIONS

Narita, Yoshio "Apparatus for separating oxygen from air" *Koatsu Gasu* 1971, 8, 314–19.
Stevens, R. K. et al. *Anal. Chem.* 1973, 45, 443A–449A.
Steffenson, D. M. et al. *Anal. Chem.* 1974, 46, 1704–1709.
Mielniczuk et al. "Photometric Detection of Oxygen" *Anal. Chem.* 1978, 50, 684–685.
Mielniczuk et al. Construction and Characteristics of a "Cold Flame" Photometric Detector *J. Chromatogr.*, 1978, 166, 1–7.
Aue et al. "A Gas Chromatographic Detector Based on the Quenching of Luminescence from a $P_4/O_2$ Cold Flame". *Can. J. Chem.*, 1979, 57, 1238–1243.
Fontijn et al. "Homogeneous Chemiluminescent Measurement of Nitric Oxide with Ozone" *Anal. Chem.*, 1970, 42, 575–579.
Yoshio Narita, Chemical Abstracts, 1972, 76:53954q.
Aldrich Catalog 1988, Aldrich Chemical Company, Inc, Milwaukee, Wisconsin pp. 1158–1159.

Primary Examiner—Jill A. Johnston
Assistant Examiner—A. Soderquist
Attorney, Agent, or Firm—Lowe, Price, LeBlanc & Becker

[57] ABSTRACT

The present invention relates to a method and an apparatus for measuring trace quantity of oxygen in a gas by reacting yellow phosphorus vapor and oxygen in a sample gas, and measuring the intensity of the light emitted by the reaction. Together with the sample gas, a constant amount of oxygen is continuously supplied to a reaction chamber so as to react with the yellow phosphorus vapor, and the intensity of the light emitted is measured. The oxygen concentration in the sample gas is determined from the difference between the value measured as above and the intensity of the light emitted by the reaction between the yellow phosphorus vapor and the added oxygen, or from the oxygen concentration obtained from the measured value and the concentration of the added oxygen. The constant amount of oxygen to be added is supplied by supplying a constant amount of a preliminarily prepared oxygen-containing gas together with the sample gas or by providing an oxygen permeating membrane in the yellow phosphorus vapor supplying system so as to supply the oxygen by the permeation of the oxygen in atmosphere. The small amount of oxygen with a concentration of several ppb in the sample gas can be continuously measured with high precision.

19 Claims, 6 Drawing Sheets

METHOD FOR MEASURING TRACE QUANTITY OF OXYGEN IN GAS

TECHNICAL FIELD

The present invention relates to a method and an apparatus for measuring trace quantity of oxygen in sample gas. More particularly, the present invention relates to a method and an apparatus for measuring trace quantity of oxygen in gas employing luminous reaction between the trace quantity of oxygen in the sample gas and yellow phosphorus vapor.

BACKGROUND ART

For measuring the concentration of trace quantity of oxygen in an industrial gas such as nitrogen, hydrogen, argon or helium, the luminous reaction between oxygen and yellow phosphorus vapor is employed. The intensity of light generated by the reaction is measured by a photodetector such as a photomultiplier. The yellow phosphorus vapor is conventionally obtained by the sublimation of solid yellow phosphorus at room temperature (15°-25° C.).

A method and an apparatus for measuring trace quantity of oxygen in a gas using the yellow phosphorus vapor are described in, for example, Japanese Laid Open Patent Application (Kokai) No. 63-302348. These will now be described referring to FIGS. 7 and 8.

An apparatus for measuring trace quantity of oxygen in a gas shown in FIG. 7 comprises a reaction chamber 10, a sample gas supplying duct 11 for supplying the sample gas to the reaction chamber 10, a yellow phosphorus vapor supplying duct 13 for supplying the yellow phosphorus vapor to the reaction chamber 10, which is generated from solid phosphorus P contained in a yellow phosphorus container 12, a photodetector 14 such as a photomultiplier for measuring the intensity of the light generated by the reaction between the oxygen in the sample gas and the yellow phosphorus vapor in the sample gas in the reaction chamber 10.

The quantity of oxygen in the sample gas is detected by supplying the sample gas through the sample gas supplying pipe 11 to the reaction chamber 10 and simultaneously supplying yellow phosphorus vapor generated from the solid yellow phosphorus P to the reaction chamber 10 through the yellow phosphorus vapor supplying duct 13 so as to allow a reaction between the yellow phosphorus vapor and the oxygen in the sample gas, followed by measuring the intensity of the light generated by the reaction by a photodetector 14 so as to determine the oxygen concentration based on the output from the photodetector.

An apparatus for measuring trace quantity of oxygen in a gas shown in FIG. 8 comprises a reaction chamber 15, a sample gas supplying pipe 11 for supplying the sample gas to the reaction chamber 15, a container 16 provided in the reaction chamber 15 for harboring solid yellow phosphorus P, a photodetector 14 such as a photomultiplier for measuring the intensity of light emitted by the reaction between the yellow phosphorus vapor and the oxygen in the sample gas.

The quantity of oxygen in the sample gas is measured by reacting the yellow phosphorus vapor sublimated in the reaction chamber 15 and the oxygen in the sample gas so as to emit light, and by measuring the intensity of the light emitted by the reaction.

However, in the application fields of industrial gases, for example, in the field of semiconductor, it is demanded to accurately determine the oxygen level in a gas to be used in the order of ppb.

Although the trace quantity of oxygen may be determined in the order of 1 ppm or less by the above-described conventional method and apparatus by controlling the amount of the yellow phosphorus, it is difficult to detect the extremely small amount of oxygen with a level of several ppb or less with high precision by the conventional method and apparatus.

DISCLOSURE OF THE INVENTION

An object of the present invention is to provide a method and an apparatus for measuring extremely small amount of oxygen contained in a sample gas at a level of several ppb or less with high precision.

Another object of the present invention is to provide a method and an apparatus for measuring trace quantity of oxygen contained in a gas by measuring the quantity of oxygen after adding a constant amount of oxygen into the sample gas, thereby measuring the quantity of oxygen in the sample gas before the addition of oxygen at a level of several tens ppb or less, particularly 30 ppb or less or even several ppb or less with high precision.

Still another object of the present invention is to provide a method and apparatus for measuring trace quantity of oxygen in a gas which excels in reproducibility and stability, which make it possible to continuously determining oxygen in a number of sample gases by continuously adding a constant amount of oxygen.

Still another object of the present invention is to provide a method and apparatus for measuring trace quantity of oxygen in a gas in which a constant amount of oxygen can be provided by supplying the oxygen to the sample gas through an oxygen permeating membrane so that there is no need to separately provide oxygen to be added, by which oxygen may be measured stably and continuously by an apparatus with simple structure.

According to the first aspect of the present invention, there is provided a method for measuring trace quantity of oxygen in a gas by reacting yellow phosphorus vapor with oxygen in a sample gas and measuring the quantity of the oxygen contained in the sample gas based on the intensity of light emitted by the reaction, characterized in that a constant amount of adding oxygen is continuously supplied together with the sample gas and the intensity of the light emitted by the reaction between the oxygen and yellow phosphorus is measured.

According to the second aspect of the present invention, there is provided a method for measuring trace quantity of oxygen in a gas characterized in that the oxygen level is determined from the difference between the measured value obtained by the method according to the first aspect of the present invention and the light intensity emitted by the reaction between the yellow phosphorus vapor and the added oxygen.

According to the third aspect of the present invention, there is provided a method for measuring trace quantity of oxygen in a gas characterized in that oxygen concentration corresponding to the measured value obtained by the method according to the first aspect of the present invention is determined, and the oxygen concentration in the sample gas is calculated by subtracting the concentration of the added oxygen from the thus determined oxygen concentration.

According to the fourth aspect of the present invention, there is provided an apparatus for measuring trace quantity of oxygen in a gas, comprising a reaction chamber in which yellow phosphorus vapor and oxygen in a sample gas are reacted, and photodetecting means for measuring intensity of light emitted by the reaction, characterized in that the apparatus further comprises a sample gas supplying pipe for supplying the sample gas to the reaction chamber, a yellow phosphorus vapor supplying pipe for supplying yellow phosphorus vapor to the reaction chamber, and an oxygen supplying pipe for supplying an oxygen-containing gas to the sample gas supplying pipe or to the reaction chamber.

According to the fifth aspect of the present invention, there is provided an apparatus for measuring trace quantity of oxygen characterized by comprising an oxygen permeating membrane in the oxygen supplying pipe according to the fourth aspect of the present invention.

According to the sixth aspect of the present invention, there is provided an apparatus for measuring trace quantity of oxygen in a gas, comprising a reaction chamber in which yellow phosphorus vapor and oxygen in a sample gas are reacted, and photodetecting means for measuring intensity of light emitted by the reaction, characterized in that the apparatus further comprises a sample gas supplying pipe for supplying the sample gas to the reaction chamber, a yellow phosphorus vapor supplying pipe for supplying yellow phosphorus vapor to the reaction chamber, and an oxygen permeating membrane provided in the sample gas supplying pipe or in the yellow phosphorus supplying pipe.

According to the seventh aspect of the present invention, there is provided an apparatus for measuring trace quantity of oxygen in a gas, characterized in that the oxygen permeating membrane employed in the apparatus according to the fifth or sixth aspect of the present invention is placed in a thermostatic bath.

By adding a constant amount of oxygen, the oxygen concentration subjected to the reaction can be controlled to the optimum range in the calibration curve of the photomeasuring means such as a photodetector, so that extremely small amount of oxygen may be measured with high precision. By adding the oxygen through an oxygen permeating membrane, a constant amount of oxygen may readily be added. Further, by controlling the temperature of the environment of the oxygen permeating membrane by placing the membrane in a thermostatic bath, the amount of the oxygen to be added can be controlled.

BRIEF DESCRIPTION OF THE INVENTION

FIG. 1 is a system diagram showing an embodiment in which a constant amount of oxygen-containing gas is added to the sample gas or to the reaction chamber.

FIG. 2 is a system diagram showing an embodiment in which a constant amount of oxygen is supplied through an oxygen permeating membrane.

FIG. 3 is a system diagram showing another embodiment in which a constant amount of oxygen is supplied through an oxygen permeating membrane.

BEST MODE FOR CARRYING OUT THE INVENTION

Figure 1:
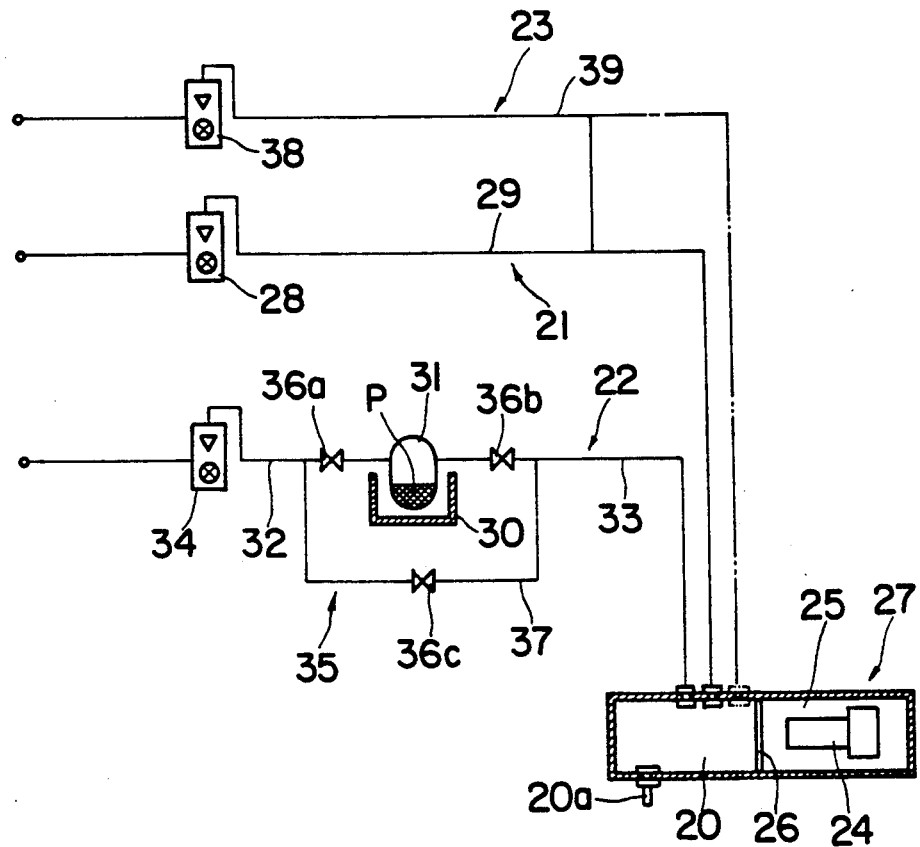
FIGS. 1-3 show embodiments of the present invention.

In the present invention, oxygen in a sample gas and a constant amount of oxygen continuously added to the sample gas react with yellow phosphorus vapor in a reaction chamber. Oxygen spontaneously reacts with yellow phosphorus upon contact therewith to emit light. Since the intensity of the light emitted by the reaction is proportional to the amount of the oxygen supplied to the reaction chamber, the amount of the oxygen can be determined by measuring the intensity of the light. The measurement of the intensity of the light may be carried out by using conventional photodetecting means such as a photomultiplier.

Controlled amount of the sample gas is supplied to the reaction chamber through a sample gas supplying pipe.

The yellow phosphorus vapor may be obtained by sublimation of solid yellow phosphorus at room temperature (15°-25° C.). The amount of the yellow phosphorus vapor supplied to the reaction chamber may be controlled by controlling the flow rate of a carrier gas for yellow phosphorus vapor and/or the temperature of the solid phosphorus. The carrier gas for yellow phosphorus vapor may preferably be inert to yellow phosphorus and must not substantially contain oxygen. Examples of the carrier gas for yellow phosphorus vapor include inert gases such as nitrogen, argon and helium, and hydrogen. If oxygen is contained in the carrier gas for yellow phosphorus vapor, the carrier gas should be used after deoxidation.

Means for continuously supplying a constant amount of oxygen to the sample gas is largely classified into two groups.

The first means is for supplying a controlled amount of pure oxygen or an oxygen-containing gas containing a constant amount of oxygen to the reaction chamber through an oxygen supplying pipe and the sample gas supplying pipe or directly to the reaction chamber through an oxygen supplying pipe. The oxygen-containing gas may preferably be a mixed gas of a constant amount of oxygen and a gas which is inert to yellow phosphorus vapor.

The second means is for supplying a constant amount of oxygen to the gas in the sample gas supplying pipe or the yellow phosphorus vapor supplying pipe by providing an oxygen permeating membrane in one of these pipes using the difference in the partial pressures of the oxygen in the pipe and the oxygen in atmosphere. The amount of the oxygen may be controlled by the effective area of the oxygen permeating membrane, temperature of the atmosphere or the flow rate of the gas in the pipe. In this case, a carrier gas not substantially containing oxygen is introduced into the oxygen supplying pipe. If oxygen is supplied to the yellow phosphorus vapor supplying pipe through the oxygen permeating membrane, although the luminous reaction initiates in the yellow phosphorus vapor supplying pipe, since the reaction rate is considerably slow, measurement can be properly carried out if an amount of oxygen sufficient for continuing the luminous reaction in the reaction chamber is introduced into the yellow phosphorus vapor supplying pipe.

The intensity of the light emitted in the reaction chamber is measured by photodetecting means.

The oxygen concentration in the sample gas may be determined from the difference between the thus obtained measured value and the intensity of light emitted by the reaction between the yellow phosphorus vapor and the added oxygen. Alternatively, the oxygen concentration corresponding to the measured value is determined and the oxygen concentration in the sample gas may be calculated by subtracting the concentration of the added oxygen from the thus determined oxygen concentration. More concretely, the oxygen concentration may be determined by comparing the measured value with a calibration curve as described later.

The present invention will now be described in more detail based on the embodiments shown in the drawings.

FIG. 1 is a system diagram showing the first embodiment of the apparatus for measuring trace quantity of oxygen in a gas according to the present invention.

The apparatus for measuring trace quantity of oxygen comprises a reaction chamber 20, a sample gas supplying system 21 for supplying the sample gas to the reaction chamber 20, a yellow phosphorus vapor supplying system 22 for supplying yellow phosphorus vapor to the reaction chamber 20, an oxygen supplying system 23 for supplying a constant amount of oxygen to the reaction chamber 20 and a photodetecting means 24 such as a photomultiplier for measuring the intensity of the emitted light.

The reaction chamber 20 and a measurement chamber 25 accommodating the photodetector 24 constitute a measurement unit 27 such that a single chamber is separated into the adjacent two chambers by a light transmitting plate 26 such as an optical glass. The reaction chamber 20 is air-tight and an exhaust outlet 20a for exhausting the gas after the reaction is provided therein.

The sample gas supplying system 21 comprises a sample gas supplying pipe 29 equipped with a sample gas flow meter 28 which can control the flow rate of the sample gas.

The yellow phosphorus supplying system 22 comprises a container 31 for harboring solid yellow phosphorus, which is placed in a thermostatic bath 30, a carrier gas supplying pipe 32 for supplying a carrier gas which carries yellow phosphorus vapor obtained by the sublimation of the solid phosphorus P in the container 31, a yellow phosphorus vapor supplying pipe 33 for supplying the carrier gas carrying the yellow phosphorus vapor to the reaction chamber 20, a carrier gas flow meter 34 provided in the carrier gas supplying pipe 32, which can control the flow rate of the carrier gas, and a bypass 35 connected to the carrier gas supplying pipe 32 and the yellow phosphorus vapor supplying pipe 33, which bypasses the container 31 containing the solid yellow phosphorus. The bypass 35 comprises valves 36a and 36b respectively provided upstream and downstream the container 31 containing the solid yellow phosphorus, and a bypass valve 36c provided in a bypass pipe 37. The bypass 35 can supply only the carrier gas to the reaction chamber 20. The carrier gas for the yellow phosphorus vapor is preferably inert to yellow phosphorus and must not substantially contain oxygen. Examples of the carrier gas for yellow phosphorus vapor include inert gases such as nitrogen, argon and helium, as well as hydrogen. If the carrier gas contains oxygen, the carrier gas is used after deoxidation.

The oxygen supplying system 23 comprises an oxygen supplying pipe 39 equipped with a flow meter 38 which can control the flow rate. The downstream portion of the oxygen supplying pipe 39 is connected to the sample gas supplying pipe 29 as shown in FIG. 1 by the solid line or connected directly to the reaction chamber 20 as shown in FIG. 1 by the phantom line. An oxygen-containing gas is used for supplying a constant amount of oxygen from the oxygen supplying system 23 to the reaction chamber through the sample gas supplying pipe 29 or directly to the reaction chamber. As the oxygen-containing gas, although pure oxygen may be employed, it is preferred to employ a mixed gas of a gas inert to the yellow phosphorus vapor and a constant amount of oxygen.

The operations for measuring trace amount of oxygen using the above-described apparatus will now be described.

The valves 36a and 36b in the bypass 35 are closed and the bypass valve 36c is opened, and the carrier gas for yellow phosphorus vapor is supplied to the reaction chamber 20 through the carrier gas supplying pipe 32, bypass pipe 37 and yellow phosphorus vapor supplying pipe 33 so as to purge the yellow phosphorus vapor supplying pipe 33 and the reaction chamber 20. The sample gas supplying pipe 29 and the oxygen supplying pipe 39 are also purged with a gas not containing oxygen, for example, a gas after passing through a deoxidizer.

A blank test is then carried out. That is, a gas not containing oxygen (blank gas), for example, a gas after passing through a deoxidizer, is supplied to the reaction chamber 20 from the sample gas supplying pipe 29 at a prescribed flow rate by controlling the flow rate by the sample gas flow meter 28. Simultaneously, an oxygen-containing gas (e.g., a gas prepared by adding a prescribed amount of oxygen gas to nitrogen gas so that the oxygen concentration therein is controlled) is supplied to the reaction chamber 20 from the oxygen supplying duct 39 through the sample gas supplying duct 29 or directly to the reaction chamber from the oxygen supplying pipe 39. Then the valves 36a and 36b in the bypass 35 are opened and the bypass valve 36c is closed. The carrier gas for yellow phosphorus vapor of which flow rate is controlled by the carrier gas flow meter 34 is supplied to the container 31 containing solid yellow phosphorus, which container is preliminarily kept at a prescribed temperature by the thermostatic bath 30, and the yellow phosphorus generated by the sublimation of the solid yellow phosphorus P is supplied to the reaction chamber 20 through the yellow phosphorus vapor supplying pipe 33. The yellow phosphorus vapor reacts with the oxygen contained in the oxygen-containing gas supplied to the reaction chamber 20 and a light is emitted thereby. The intensity of the emitted light is measured by the photodetector 24 and a photoelectric current corresponding to the amount of the added oxygen is outputted. Since the thus obtained output value is the output value obtained when the oxygen concentration in the sample gas is zero, zero-adjustment is carried out by setting this output value to the zero point of the oxygen concentration in the sample gas.

After conducting the zero-adjustment by the blank test as described above, the oxygen concentration in a sample gas is carried out. That is, the sample gas is supplied from the sample gas supplying pipe to the reaction chamber after controlling the flow rate to a prescribed concentration by the sample gas flow meter 28. At this time, the oxygen-containing gas and the yellow phosphorus vapor are continuously supplied to the reaction chamber 20. The oxygen in the sample gas and the oxygen-containing gas supplied to the reaction chamber 20 react with yellow phosphorus vapor in the reaction chamber, thereby emitting a light. The intensity of the emitted light is measured by the photodetector 24 and a photoelectric current is outputted.

The output value is compared with a preliminarily prepared calibration curve and the oxygen concentration in the sample gas may be obtained as a difference between the output value obtained when measuring the oxygen concentration in the sample gas and the output value in the blank test.

The measurement of the trace quantity of oxygen will now be described by way of examples.

Firstly, a calibration curve covering the expected range of the oxygen level in the sample gas is provided.

More particularly, standard gases containing oxygen in the concentration of 10 ppb, 20 ppb, 30 ppb, 40 ppb, 50 ppb, 60 ppb and 70 ppb, respectively, and an oxygen-containing gas with an oxygen concentration of 360 ppb are provided. Firstly, nitrogen gas after passing through a deoxidizer (blank gas) is supplied to the reaction chamber through the sample gas supplying system 21 at a flow rate of 800 ml/min, nitrogen gas for carrying yellow phosphorus vapor is supplied to the reaction chamber 20 through the yellow phosphorus supplying system 22 at a flow rate of 300 ml/min, and an oxygen-containing gas with an oxygen concentration of 360 ppb is supplied to the reaction chamber 20 through the oxygen supplying system 23 at a flow rate of 100 ml/min so as to attain an oxygen concentration in the reaction chamber 20 of 30 ppb. The intensity of the emitted light in the reaction chamber 20 at this point is measured by the photodetector 24 and zero-adjustment is carried out.

Figure 4:
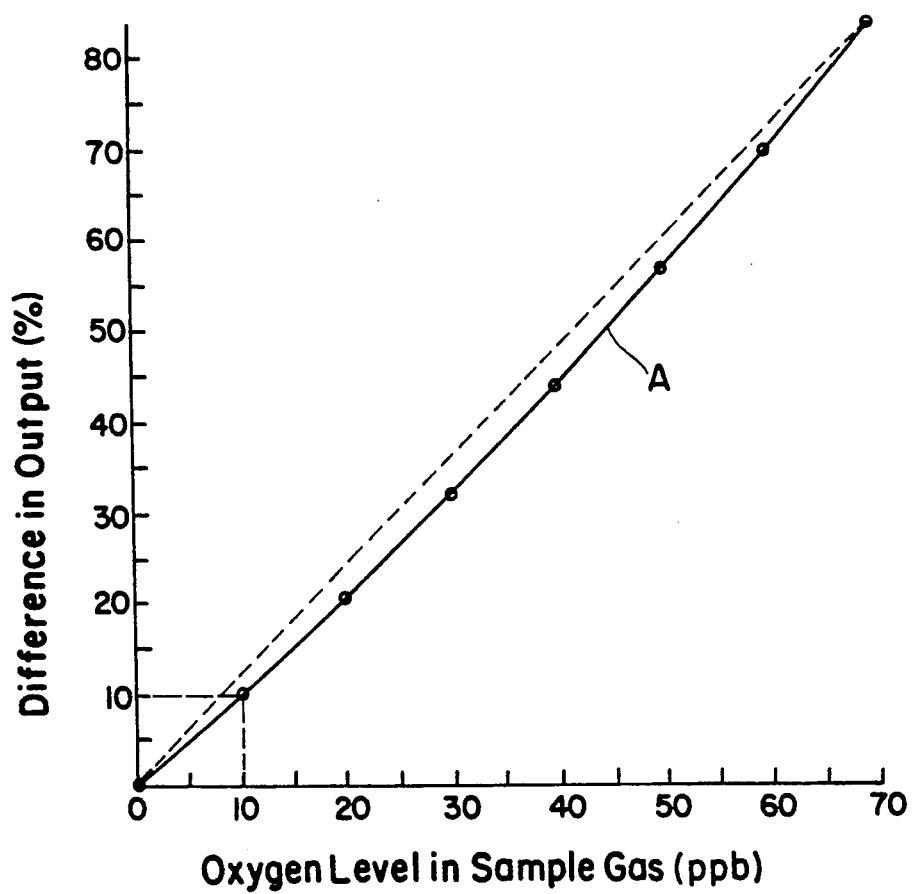
FIG. 4 shows an example of a calibration curve prepared by using a standard gas containing a known concentration of oxygen and an oxygen-containing gas to which a constant amount of oxygen is added employing the apparatus shown in FIG. 1.

A standard gas with an oxygen concentration of 10 ppb is then supplied to the reaction chamber through the sample gas supplying system 21 in place of the blank gas. At this time, the nitrogen gas carrying the yellow phosphorus vapor and the oxygen-containing gas are continuously supplied to the reaction chamber 20. The intensity of the light emitted from the reaction chamber 20 is measured by the photodetector 24 and the obtained output value is plotted. In the same manner, the output values obtained by using the standard gases with oxygen levels of 20 ppb-70 ppb are plotted. By connecting the plotted points with a line, a calibration curve A shown in FIG. 4 corresponding to the oxygen concentrations of 0 ppb to 70 ppb is obtained. Thus, in the calibration curve A, the output obtained when the oxygen level in the reaction chamber 20 is 30 ppb corresponds to the oxygen concentration of 0 ppb in the sample gas. In FIG. 4, the abscissa indicates the oxygen concentration in the standard gas, and the ordinate indicates the difference in terms of percent between the output obtained by using the standard gas and the output employed for the zero-adjustment.

It should be noted that since the oxygen contained in the standard gas is diluted and mixed with the nitrogen gas carrying the yellow phosphorus vapor and the oxygen-containing gas in the reaction chamber 20, for example, when the standard gas with an oxygen concentration of 10 ppb is supplied to a reaction chamber 20, the oxygen concentration in the reaction chamber 20 is 36.7 ppb.

After preparing the calibration curve A, measurement of the oxygen concentration in the sample gas is carried out. That is, the nitrogen gas carrying the yellow phosphorus vapor and the oxygen-containing gas are supplied to the reaction chamber in the manner described above, and simultaneously a sample gas with an oxygen level of x is supplied to the reaction chamber through the sample gas supplying system 21 at a flow rate of 800 ml/min. The output from the photodetector 24 is measured and the oxygen concentration is determined based on the calibration curve A. For example, if the output difference is 10%, the oxygen concentration in the sample gas is determined to 10 ppb from the calibration curve A.

Since the oxygen in the sample gas is diluted and mixed with the nitrogen gas carrying the yellow phosphorus vapor and with the oxygen-containing gas in the reaction chamber, for example, if a sample gas with an oxygen concentration of 10 ppb is supplied to the reaction chamber 20, the oxygen concentration in the reaction chamber 20 is 36.7 ppb. However, since the zero-adjustment is carried out when the oxygen level in the reaction chamber 20 is 30 ppb, and since the oxygen in the sample gas is diluted under the same conditions as the oxygen in the standard gases when preparing the calibration curve, the oxygen concentration in the sample gas can directly be determined from the obtained output difference.

Figure 5:
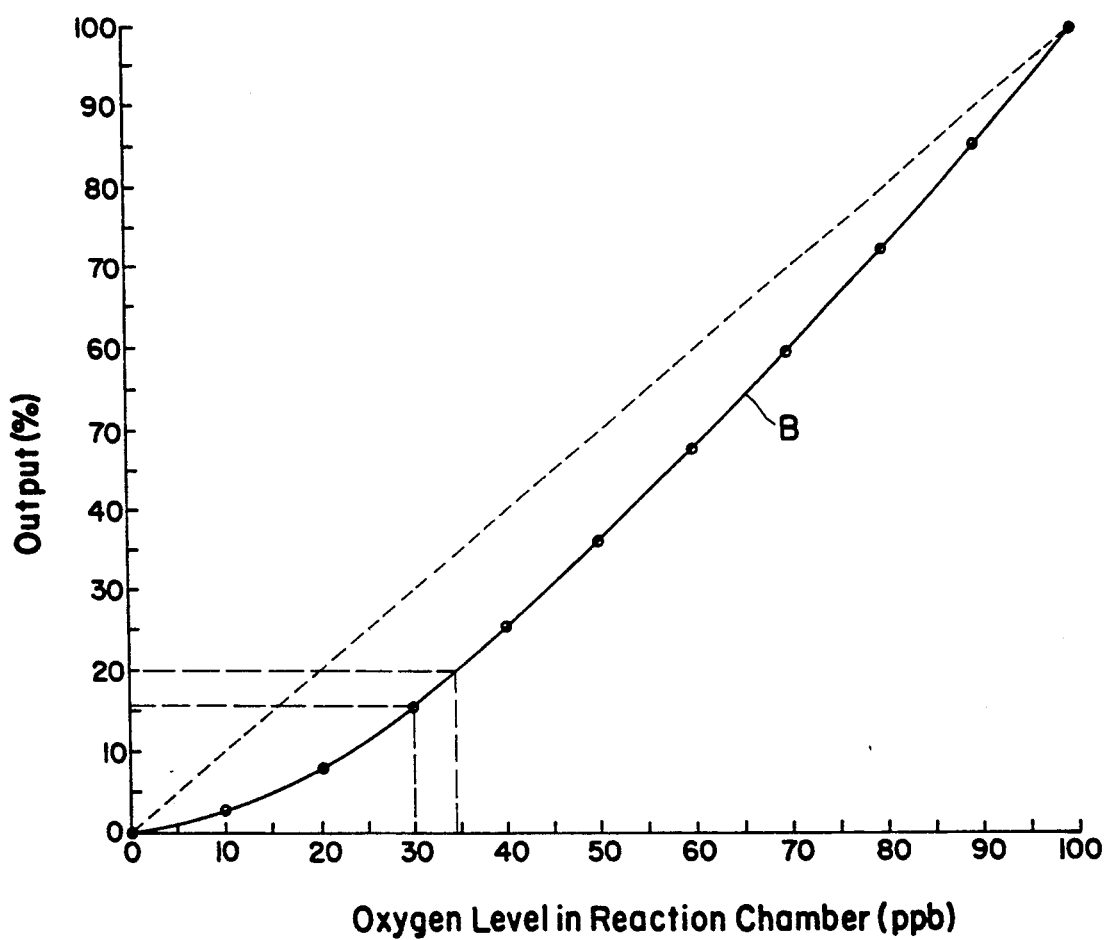
FIG. 5 is an example of a calibration curve prepared by using a standard gas containing a known concentration of oxygen employing the apparatus shown in FIG. 1.

Next, the procedures for measuring the oxygen level in the sample gas from the calibration curve based on the oxygen concentration in the reaction chamber 20 will now be described referring to FIG. 5. A calibration curve B covering the oxygen levels of 0 ppb to 100 ppb is prepared by connecting the plotted output values obtained by introducing nitrogen gas not containing oxygen into the oxygen supplying pipe 23 at a flow rate of 100 ml/min in place of the oxygen-containing gas with an oxygen concentration of 360 ppb, introducing the other gases as described above so as to carry out the zero-adjustment, supplying standard gases with known oxygen concentrations to the reaction chamber 20 through the sample gas supplying pipe 21 so as to change the oxygen concentration in the reaction chamber 20 to 10 ppb, 20 ppb, 30 ppb, 40 ppb, 50 ppb, 60 ppb, 70 ppb, 80 ppb, 90 ppb and 100 ppb, and plotting the output values. In FIG. 5, the abscissa indicates the oxygen concentration in the reaction chamber 20 and the ordinate indicates the output value in terms of percent. Thus, in the calibration curve B, the zero point in the calibration curve A, that is, the oxygen concentration in the reaction chamber 20 of 30 ppb is indicated as 16%.

The oxygen concentration in the sample gas may be determined as follows using the calibration curve B.

I. Measurement of Reference Value (Zero-adjusting value)
(a) To Sample Gas Supplying System 21
   Nitrogen gas after passing through a deoxidizer at a flow rate of 800 ml/min.
(b) To Yellow Phosphorus Supplying System 22
   Carrier gas for yellow phosphorus vapor (nitrogen gas) at a flow rate of 300 ml/min.
(c) To Oxygen-supplying System 23
   Nitrogen gas containing 360 ppb of oxygen at a flow rate of 100 ml/min.

Therefore, the oxygen concentration in the reaction chamber is 30 ppb, and the output of the photodetector at this point is 16% as shown in FIG. 5. This output is defined as the output of the sample gas with an oxygen level of zero.

II. Measurement of Oxygen Level in Sample Gas (a) To Sample Gas Supplying System 21

Sample gas with an oxygen concentration of x ppb at a flow rate of 800 ml/min.

(b) To Yellow Phosphorus Vapor Supplying System 22

Carrier gas (nitrogen gas) for yellow phosphorus vapor at a flow rate of 300 ml/min.

(c) To Oxygen Supplying System 23

Nitrogen gas containing 360 ppb of oxygen in nitrogen at a flow rate of 100 ml/min.

The oxygen concentration c ppb in the reaction chamber 20 is represented by the formula:

$$c = \left(30 + \frac{800}{1200} x\right)$$

If the output value from the photodetector at this point is 20%, the oxygen concentration in the reaction chamber 20 corresponding to the output value of 20% is 34.5 ppb as determined from the calibration curve B in FIG. 5.

By substituting c in the above equation for 34.5, an equation of $$34.5 = \left(30 + \frac{800}{1200} x\right)$$

is obtained.

By solving this equation, x is 6.75, so that the oxygen level x to be determined in the sample gas is 6.75 ppb.

In cases where measurement is carried out according to the above-described procedures, memory function and processing function are provided in the analyzer (the measuring apparatus of the present invention), and the calibration curve and the calculation are so constituted as to automatically calculate the measured values and to display them by means of these functions. In this case, the oxygen concentration in the sample gas may be determined from the output difference of the photodetector or by measuring the oxygen concentration after addition of oxygen and subtracting the added oxygen concentration from the measured oxygen concentration.

Thus, the oxygen concentration in the sample gas may also be determined by determining the total concentration of the oxygen supplied to the reaction chamber 20 from the sample gas supplying system 21 and the oxygen supplying system 23, and calculating the difference between the thus measured oxygen concentration and the concentration of the added oxygen.

As is apparent from the calibration curve shown in FIG. 5, by making the oxygen concentration in the reaction chamber 20 to not less than 30 ppb by continuously adding oxygen with a concentration of 30 ppb to the reaction chamber 20 as mentioned above, even if the oxygen concentration in the sample gas is about 5 ppb, output difference of about 5% is obtained, so that the measurement of the oxygen concentration in the sample gas can be sufficiently carried out. On the other hand, if no oxygen is added to the reaction chamber 20, even if the oxygen level in the sample gas is about 10 ppb, output difference of about only 2-3% is obtained, which cannot be distinguished from noise of the photodetector 24. Thus, in the calibration curve used in the present invention, the output difference corresponding to the oxygen level in the sample gas of not more than 20 ppb is made large, so that extremely small amount of oxygen may be measured with high precision.

Thus, by continuously adding oxygen with a concentration of, for example, 30 ppb to the reaction chamber 20, the oxygen level measured by the measurement unit 27 may be adjusted to the range optimum for the photodetector 24, so that the trace quantity of oxygen in the sample gas at a concentration of several ppb may be determined accurately with high precision.

Figure 2:
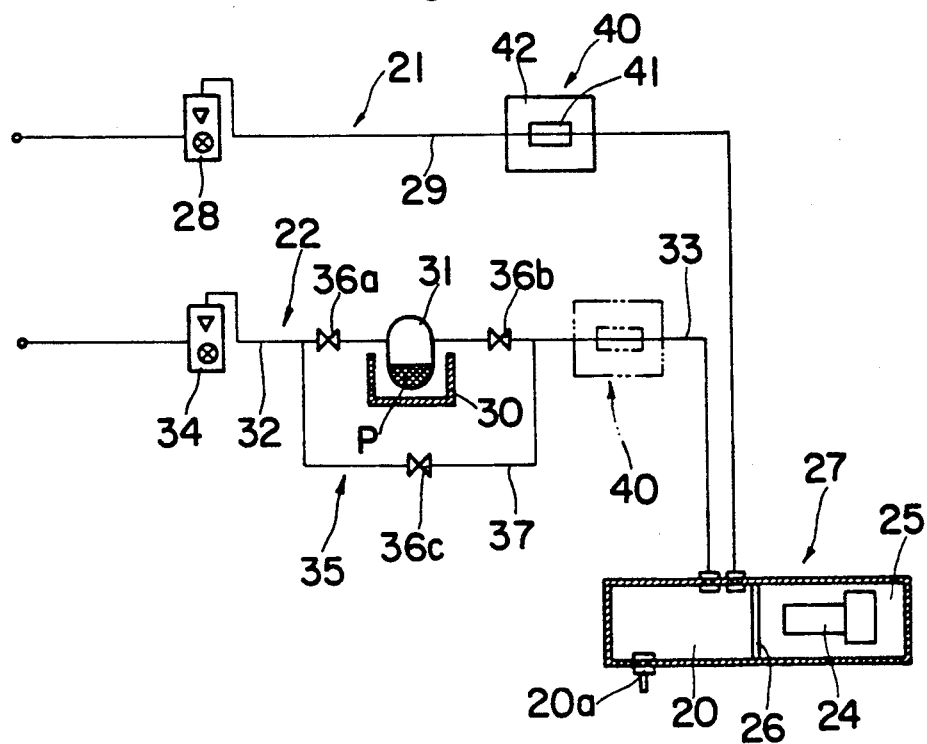
Figure 3:
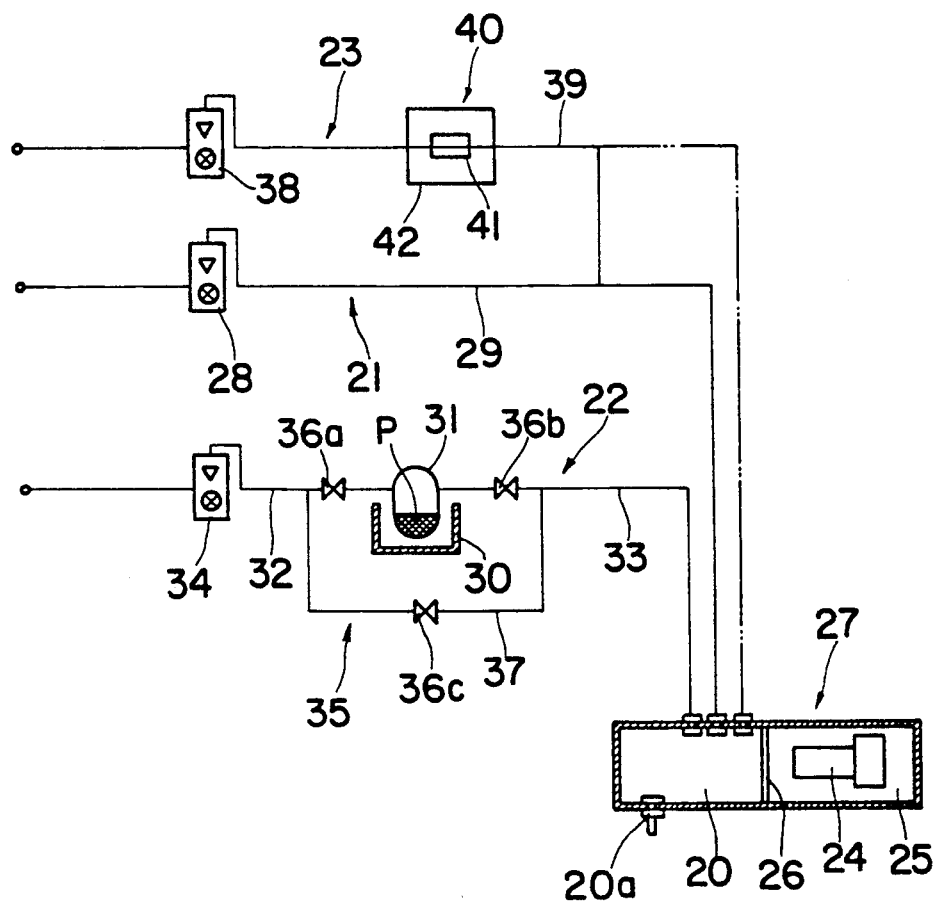

FIGS. 2 and 3 shows different embodiments in which oxygen to be added to the sample gas is obtained by an oxygen permeating membrane. It should be noted that the same reference numerals are used for denoting the same elements as in FIG. 1 and the explanations thereof are omitted here.

The apparatus for measuring trace quantity of oxygen shown in FIG. 2 comprises a reaction chamber 20, a sample gas supplying system 21, a yellow phosphorus vapor supplying system 22 and a photodetector 24 such as a photomultiplier for measuring the light intensity, as in the apparatus shown in FIG. 1, but the oxygen supplying system 23 shown in FIG. 1 is not provided.

An oxygen introducing unit 40 is provided in the sample gas supplying pipe 29 in the sample gas supplying system 21 or in the yellow phosphorus vapor supplying pipe 33 in the yellow phosphorus vapor supplying system 22.

The oxygen introducing unit 40 comprises a tubular oxygen permeating membrane 41 and a thermostatic bath 42 for keeping the temperature of the environment of the oxygen permeating membrane 41 at a prescribed temperature, which contains therein the oxygen permeating membrane 41. The oxygen permeating membrane 41 is prepared by forming a material which permeates oxygen into tubes. Examples of the material which permeates oxygen include synthetic resins such as Teflon (trade name), ceramics such as zirconia, various rubbers, carbon-based membranes and ion pumps.

By providing the oxygen introducing unit 40 in the sample gas supplying pipe 29 or in the yellow phosphorus vapor supplying pipe 33, a constant amount of oxygen may be introduced into the sample gas or into the carrier gas for yellow phosphorus vapor by exploiting the difference between the partial oxygen pressure in the oxygen permeating membrane 41 and the partial oxygen pressure in atmosphere.

The environment in the thermostatic bath 42, that is, the environment of the oxygen permeating membrane 41 may be atmosphere air and the amount of the oxygen to be introduced may be controlled by controlling the surface area of the oxygen permeating membrane 41, the temperature of the atmosphere thereof, flow rate or pressure of the gas in the pipe.

It should be noted that in cases where the oxygen introducing unit 40 is provided in the yellow phosphorus vapor supplying pipe 33, although luminescence initiates at the downstream portion of the oxygen introducing unit 40 by the reaction between the oxygen and the yellow phosphorus, since the reaction rate is considerably slow, by introducing oxygen in an amount sufficient to continue the reaction in the reaction chamber 20, the same effect obtained by introducing oxygen by another means can be obtained.

By merely providing an oxygen permeating membrane 41 made of Teflon or the like in the pipe for supplying the gas into the reaction chamber 20 and placing the same in the thermostatic bath 42, a constant amount of oxygen with a concentration of as small as several tens ppb may be added with such a very simple structure. Further, throughout the operation of the apparatus for measuring trace quantity of oxygen, oxygen may readily be provided stably and continuously without the need for separately providing oxygen to be added as in the apparatus shown in FIG. 1, so that the measurement may be carried out continuously for long period of time at a lower cost.

The measurement of trace quantity of oxygen will now be described concretely based on experimental examples.

A tubular oxygen permeating membrane 41 made of Teflon was provided in the sample gas supplying pipe 29 and was placed in the thermostatic bath 42. The Teflon tube is commercially available and had an inner diameter of 1.59 mm, outer diameter of 3.17 mm and a length of 20 mm. To make the amount of oxygen added to the sample gas through the oxygen permeating membrane 41 constant, it is necessary to make the supplying pressure of the sample gas and the flow rate constant and to place the oxygen permeating membrane 41 in the thermostatic bath 42 so as to make the temperature of the gas in and out of the oxygen permeating membrane 41 constant. In this experimental example, the outer environment of the oxygen permeating membrane 41 was atmosphere and the temperature in the thermostatic bath 42 was set to 50° C.

Although the pressure in the tube of the oxygen permeating membrane is somewhat higher than the pressure outside the membrane (by about the pressure loss in the duct), since the oxygen concentration is higher outside the tube than inside the tube, very small amount of oxygen in atmosphere permeates the membrane due to the difference in this partial oxygen pressures and is mixed with the sample gas flowing the pipe. In this case, in order to make the amount of the oxygen added to the sample gas through the oxygen permeating membrane 41 constant, it is necessary to make the supplying pressure and the flow rate of the sample gas constant, and to make the temperature of the oxygen permeating membrane 41 and of the gas inside and outside the pipe constant. In this experimental example, the parameters are set such that 30 ppb of oxygen is continuously supplied to the sample gas when the sample gas is supplied at a flow rate of 800 ml/min.

Figure 6:
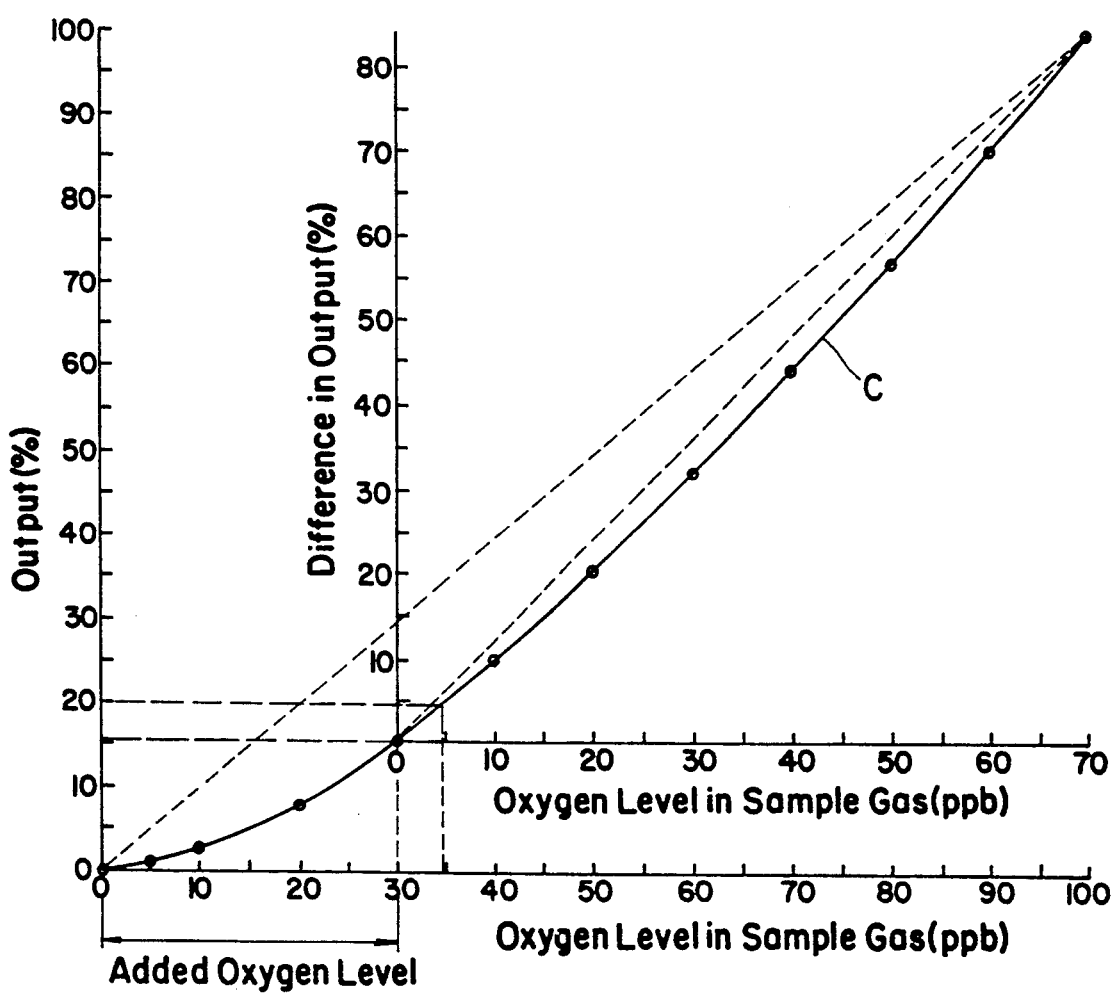
FIG. 6 is an example of a calibration curve prepared by using a standard gas containing a known concentration of oxygen employing the apparatus shown in FIG. 2.
Figure 7:
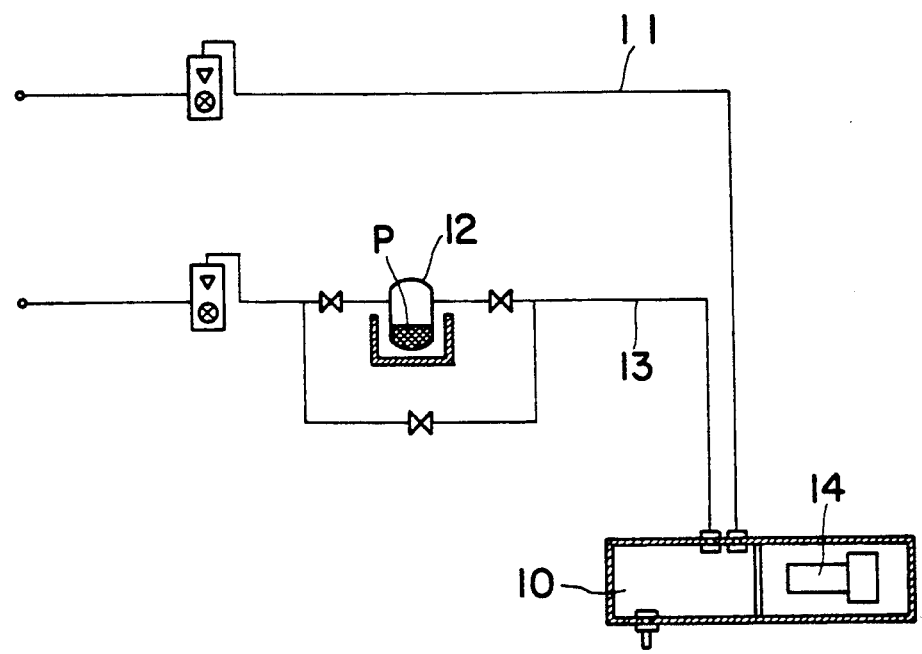
FIGS. 7 and 8 are system diagrams each showing a conventional apparatus for measuring trace amount of oxygen.
Figure 8:
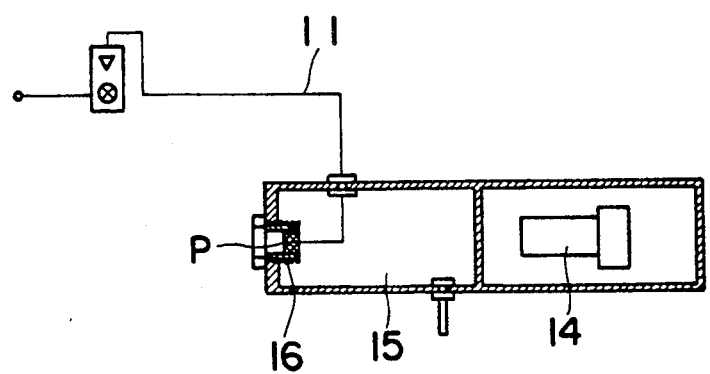

As in the above-described experimental example, standard gases with oxygen concentrations of 10 ppb, 20 ppb, 30 ppb, 40 ppb, 50 ppb, 60 ppb and 70 ppb, respectively, were supplied to the reaction chamber 20 through the sample gas supplying pipe 29 at a flow rate of 800 ml/min, and nitrogen gas carrying a prescribed amount of yellow phosphorus vapor was simultaneously supplied to the reaction chamber 20 through the yellow phosphorus vapor supplying pipe 29 at a flow rate of 300 ml/min. The output values obtained by using the standard gases were plotted and the plotted points were connected with a line, which is a calibration curve C shown in FIG. 6.

Since the calibration curve C was prepared in the conditions in which 30 ppb of oxygen was continuously admixed with the standard gases through the oxygen permeating membrane 41, this calibration curve corresponds to the range of 30 ppb-100 ppb or the output value of 16%-100% of the calibration curve prepared by using a gas in which oxygen is not admixed. That is, if a standard gas containing 10 ppb of oxygen is supplied at a flow rate of 800 ml/min, the reaction chamber 20 is in such a condition that a gas containing 40 ppb of oxygen is supplied to the reaction chamber at a flow rate of 800 ml/min.

After preparing the calibration curve C as mentioned above, the measurement of the oxygen concentration in the sample gas is carried out. That is, nitrogen gas carrying the yellow phosphorus vapor is supplied to the reaction 20 as described above, and a sample gas with an oxygen level of x is supplied to the reaction chamber 20 through the sample gas supplying system 21 at a flow rate of 800 ml/min. The output of the photodetector 24 at this point is read and the oxygen concentration is determined based on the calibration curve C. For example, if the output difference is 4%, the oxygen concentration in the sample gas is determined to be 4.5 ppb from the calibration curve C. Alternatively, using the calibration curve obtained by using a gas to which oxygen is not admixed, the oxygen level of 34.5 ppb is determined from the output value of 20% and then the oxygen concentration of 4.5 ppb in the sample gas may be determined by subtracting the oxygen concentration of the added oxygen of 30 ppb from the oxygen concentration of 34.5 ppb.

With the apparatus in which the oxygen introducing unit is provided in the yellow phosphorus vapor supplying system 22, the oxygen concentration in the sample gas may be determined in the same manner.

The apparatus for measuring trace amount of oxygen shown in FIG. 3 has the similar constitution to the apparatus shown in FIG. 1, which further comprises an oxygen introducing unit 40 in the oxygen supplying pipe 39 in the oxygen supplying system 23. It should be noted that a carrier gas for oxygen which is an inert gas substantially not containing oxygen is supplied to the oxygen supplying pipe 39.

By providing the oxygen introducing unit 40 in the oxygen supplying pipe 39, a constant amount of oxygen may be added to the carrier gas for oxygen. Therefore, as the apparatus shown in FIG. 1, a constant amount of oxygen may be continuously supplied to the reaction chamber 20 from the oxygen supplying pipe 39 directly or through the sample gas supplying pipe 29.

In cases where the oxygen introducing unit 40 is provided in the oxygen supplying pipe 39, by controlling the flow rate of the carrier gas for oxygen, the amount of the oxygen added through the oxygen permeating membrane 41 may be controlled, so that an optimum amount of oxygen may be added depending on the oxygen level in the sample gas.

In carrying out the measurement of the trace quantity of oxygen in a sample gas with this apparatus, the measurement may be carried out in the same manner as with the apparatus shown in FIG. 1. That is, by setting the flow rate of the carrier gas for oxygen to 100 ml/min and by setting the amount of oxygen added through the oxygen permeating membrane 41 to 360 ppb, the trace quantity of oxygen in the sample gas may be determined in the same manner as described above.

Although the invention was described in detail based on specific embodiments thereof, it is apparent for those skilled in the art that various modifications may be made without departing from the spirit and scope of the present invention. For example, the apparatus may be provided with a function for indicating the measured values in terms of the above-described output difference or with a recorder in which a function for obtaining the difference in concentrations is preliminarily incorporated, or the apparatus may be designed as an alarm. Therefore, the above description must not be interpreted in any restrictive way.

We claim:

1. In a method for measuring a trace quantity of oxygen in a gas comprising reacting yellow phosphorus vapor with the oxygen in a sample of said gas to provide light and measuring the quantity of the oxygen in the sample of said gas based on the measured intensity of the light emitted by the reaction, said measured intensity having a non-linear detector response in the range of 0–100 parts-per-billion wherein the improvement comprises continuously supplying a constant amount of oxygen together with the sample of the gas, the amount of oxygen continuously supplied being effective to shift the intensity of the light emitted by the reaction to a range in which the non-linear detector response is substantially removed wherein the measured intensity is the light emitted by the reaction of the yellow phosphorus vapor and both the oxygen in the sample and the oxygen continuously supplied with the sample.

2. The method for measuring a trace quantity of oxygen in a gas according to claim 1, wherein the light emitted by the reaction between the the yellow phosphorus vapor and both the oxygen continuously supplied and the oxygen in the sample is measured by a photodetector and the oxygen concentration is determined from the output of the photodetector.

3. The method for measuring a trace quantity of oxygen in a gas according to claim 1, wherein the constant amount of oxygen is continuously supplied by supplying an oxygen-containing gas containing the constant amount of oxygen.

4. The method for measuring a trace quantity of oxygen in a gas according to claim 1, wherein the constant amount of oxygen to be continuously supplied is supplied to the sample gas or to a carrier gas for yellow phosphorus vapor through an oxygen permeating membrane.

5. The method for measuring a trace quantity of oxygen in a gas according to claim 4, wherein the amount of the constant quantity of oxygen to be continuously supplied is controlled by controlling the temperature in a thermostatic bath harboring the oxygen permeating membrane by using the difference in the partial pressures of the oxygen in a pipe in which said membrane is located and the oxygen in the atmosphere, the effective area of the permeating membrane, the temperature of the atmosphere or the flow rate of the gas in the pipe.

6. The method for measuring a trace quantity of oxygen in a gas according to claim 1, wherein the constant amount of oxygen to be supplied is supplied to a carrier gas for oxygen through an oxygen permeating membrane.

7. The method for measuring a trace amount of oxygen in a gas according to claim 6, wherein the amount of the constant amount of oxygen to be continuously supplied is controlled by controlling the temperature in a thermostatic bath harboring the oxygen permeating membrane.

8. In a method for measuring a trace quantity of oxygen in a gas comprising reacting yellow phosphorus vapor with the oxygen in a sample of said gas to provide light and measuring the quantity of the oxygen in the sample of said gas based on the measured intensity of the light emitted by the reaction, said measured intensity having a non-linear detector response in the range of 0–100 parts-per-billion wherein the improvement comprises continuously supplying a constant amount of oxygen together with the sample of the gas, the amount of oxygen continuously supplied being effective to shift the intensity of the light emitted by the reaction to a range in which the non-linear detector response is substantially removed wherein the measured intensity is the light emitted by the reaction of the yellow phosphorus vapor and both the oxygen in the sample and the oxygen continuously supplied with the sample and determining an oxygen concentration from the difference between the measured amount of light and an intensity emitted by a reaction between the yellow phosphorus vapor and the oxygen continuously supplied.

9. The method for measuring a trace quantity of oxygen in a gas according to claim 8, wherein the light emitted by the reaction between the yellow phosphorus vapor and both the oxygen continuously supplied and the oxygen in the sample is measured by a photodetector and the oxygen concentration is determined from the output of the photodetector.

10. The method for measuring a trace quantity of oxygen in a gas according to claim 8, wherein the constant amount of oxygen is continuously supplied by supplying an oxygen-containing gas containing the constant amount of oxygen.

11. The method for measuring a trace quantity of oxygen in a gas according to claim 8, wherein the constant amount of oxygen to be continuously supplied is supplied to the sample gas or to a carrier gas for yellow phosphorus vapor through an oxygen permeating membrane located in a pipe by using the difference in the partial pressures of the oxygen in the pipe and the oxygen in the atmosphere, the effective area of the permeating membrane, the temperature of the atmosphere or the flow rate of the gas in the pipe.

12. The method for measuring a trace quantity of oxygen in a gas according to claim 8, wherein the constant amount of oxygen to be supplied is supplied to a carrier gas for oxygen through an oxygen permeating membrane.

13. The method for measuring a trace quantity of oxygen in a gas according to claim 8, wherein the amount of oxygen continuously supplied together with the sample is 30 ppb or less.

14. In a method for measuring a trace quantity of oxygen in a gas comprising reacting yellow phosphorus vapor with the oxygen in a sample of said gas to provide light and measuring the quantity of the oxygen in the sample of said gas based on the measured intensity of the light emitted by the reaction, said measured intensity having a non-linear detector response in the range of 0–100 parts-per-billion wherein the improvement comprises continuously supplying a constant amount of oxygen together with the sample of the gas, the amount of oxygen continuously supplied being effective to shift the intensity of the light emitted by the reaction to a range in which the non-linear detector response is substantially removed wherein the measured intensity is the light emitted by the reaction of the yellow phosphorus vapor and both the oxygen in the sample and the oxygen continuously supplied with the sample;

measuring said shifted intensity;

calculating an oxygen concentration from said measured intensity of light; and calculating a difference between said oxygen concentration and the concentration of the continuously supplied oxygen.

15. The method for measuring a trace quantity of oxygen in a gas according to claim 14, wherein the light emitted by the reaction between the yellow phosphorus vapor and both the oxygen continuously supplied and the oxygen in the sample is measured by a photodetector and the oxygen concentration is determined from the output of the photodetector.

16. The method for measuring a trace quantity of oxygen in a gas according to claim 14, wherein the constant amount of oxygen is continuously supplied by supplying an oxygen-containing gas containing the constant amount of oxygen.

17. The method for measuring a trace quantity of oxygen in a gas according to claim 14, wherein the constant amount of oxygen to be continuously supplied is supplied to the sample gas or to a carrier gas for yellow phosphorus vapor through an oxygen permeating membrane located in a pipe by using the difference in the partial pressures of the oxygen in the pipe and the oxygen in the atmosphere, the effective area of the permeating membrane, the temperature of the atmosphere or the flow rate of the gas in the pipe.

18. The method for measuring trace quantity of oxygen in a gas according to claim 14, characterized in that the constant amount of oxygen to be supplied is supplies to a carrier gas for oxygen through an oxygen permeating membrane.

19. The method for measuring a trace quantity of oxygen in a gas according to claim 14, wherein the amount of oxygen continuously supplied together with the sample is 30 ppb or less.

* * * * *